(12) United States Patent
Gebert et al.

(10) Patent No.: US 10,156,256 B2
(45) Date of Patent: Dec. 18, 2018

(54) CERMET BEARING, IN PARTICULAR FOR AN IMPLANTABLE MEDICAL DEVICE

(71) Applicant: Heraeus Deutschland GmbH & Co. KG, Hanau (DE)

(72) Inventors: Jörg-Martin Gebert, Karlsruhe (DE); Ulrich Hausch, Frankfurt (DE); Stefan Schibli, Frankfurt (DE)

(73) Assignee: HERAEUS DEUTSCHLAND GMBH & CO. KG, Hanau (DE)

( * ) Notice: Subject to any disclaimer, the term of this patent is extended or adjusted under 35 U.S.C. 154(b) by 0 days.

(21) Appl. No.: 15/336,260

(22) Filed: Oct. 27, 2016

(65) Prior Publication Data

US 2017/0122373 A1    May 4, 2017

(30) Foreign Application Priority Data

Nov. 4, 2015    (EP) .................................... 15193023

(51) Int. Cl.
*F16C 33/04*    (2006.01)
*A61M 1/10*    (2006.01)
(Continued)

(52) U.S. Cl.
CPC ........... *F16C 33/043* (2013.01); *A61M 1/101* (2013.01); *A61M 1/1013* (2014.02);
(Continued)

(58) Field of Classification Search
CPC ........ F16C 17/02; F16C 17/08; F16C 33/043; F16C 2202/04; F16C 2202/20;
(Continued)

(56) References Cited

U.S. PATENT DOCUMENTS 5,306,677 A * 4/1994 Newkirk ................. C04B 35/10
                                                                   501/102
6,315,830 B1 * 11/2001 Nakagawa ................ C23C 2/00
                                                                   118/423
(Continued)

FOREIGN PATENT DOCUMENTS

DE           19625300 A1    1/1998
DE       112006002413 T5    6/2008
(Continued)

OTHER PUBLICATIONS

Schima, et al. "In-vitro-Teststand für die Untersuchung der Thrombenbildung in Blutpumpen und anderen blutkontaktierten Systemen" in Biomedizinische Technik Band 57, Ergänzungsband 1, 1992, S. 266-268.

*Primary Examiner* — Marcus Charles
(74) *Attorney, Agent, or Firm* — Blank Rome LLP

(57) ABSTRACT

A mechanical bearing contains a first component and a further component, wherein the mechanical bearing is designed such that the first component and the further component are able to execute a bearing movement relative to each other, wherein the first component or the further component contains a cermet or both contain a cermet. The invention further relates to an implantable medical device containing the mechanical bearing, in particular to a blood pump, and also to a use of a cermet for producing a mechanical bearing, and to a use of the mechanical bearing for supporting a component of an implantable medical device.

7 Claims, 6 Drawing Sheets

(51) Int. Cl.
  *C22C 29/00* (2006.01)
  *C22C 29/12* (2006.01)
  *C22C 29/16* (2006.01)
  *B22F 7/06* (2006.01)
  *C22C 29/06* (2006.01)
  *A61M 1/12* (2006.01)
  *F16C 17/02* (2006.01)
  *F16C 17/08* (2006.01)

(52) U.S. Cl.
  CPC ............ *A61M 1/122* (2014.02); *A61M 1/125* (2014.02); *B22F 7/062* (2013.01); *C22C 29/06* (2013.01); *C22C 29/12* (2013.01); *C22C 29/16* (2013.01); *F16C 17/02* (2013.01); *F16C 17/08* (2013.01); *F16C 2202/04* (2013.01); *F16C 2202/20* (2013.01); *F16C 2206/80* (2013.01); *F16C 2316/18* (2013.01)

(58) Field of Classification Search
  CPC .. F16C 2202/80; F16C 2316/18; F16C 29/02; F16C 33/24; A61M 1/1013; A61M 1/101; C22C 29/12; C22C 29/16; B29C 45/66
  USPC .... 384/129, 261, 276, 279, 282, 297, 907.1, 384/912; 607/37; 174/564–565
  See application file for complete search history.

(56) References Cited

U.S. PATENT DOCUMENTS

| | | | |
|---|---|---|---|
| 7,255,690 B2 * | 8/2007 | Gray | A61M 5/14216 604/151 |
| 8,755,887 B2 * | 6/2014 | Troetzschel | A61N 1/3754 607/36 |
| 8,929,987 B2 * | 1/2015 | Troetzschel | A61N 1/3754 607/37 |
| 2004/0127852 A1 * | 7/2004 | Gray | A61M 5/14216 604/151 |
| 2010/0047434 A1 * | 2/2010 | Kumar | C23C 24/103 427/2.1 |
| 2010/0143620 A1 * | 6/2010 | Ajdelsztajn | B22F 5/009 428/34.5 |
| 2011/0190885 A1 * | 8/2011 | Troetzschel | A61F 2/02 623/11.11 |
| 2012/0193117 A1 * | 8/2012 | Specht | A61N 1/3754 174/50.53 |
| 2012/0193141 A1 * | 8/2012 | Reisinger | A61N 1/3752 174/659 |
| 2012/0203294 A1 * | 8/2012 | Troetzschel | A61N 1/3754 607/5 |
| 2015/0165219 A1 * | 6/2015 | Markham | A61N 1/3754 607/116 |

FOREIGN PATENT DOCUMENTS

| | | | | |
|---|---|---|---|---|
| DE | 102009035971 A1 | | 2/2011 | |
| DE | 102010006689 A1 | | 9/2011 | |
| JP | 01196712 A | * | 8/1989 | ............... G11B 5/52 |
| JP | 02085519 A | * | 3/1990 | ............... F16C 33/24 |
| JP | 05044002 A | * | 2/1993 | ............... F16C 13/02 |
| JP | 05087145 A | * | 4/1993 | ............... F16C 33/24 |
| JP | 08281748 A | * | 10/1996 | ............... F16C 29/02 |
| JP | 2004003633 A | | 1/2004 | |
| JP | 2004330455 A | * | 11/2004 | ............... F16C 33/043 |
| WO | WO-9800185 A1 | | 1/1998 | |

* cited by examiner

100

106

109

400

600

CERMET BEARING, IN PARTICULAR FOR AN IMPLANTABLE MEDICAL DEVICE

CROSS-REFERENCES TO RELATED APPLICATIONS

This non-provisional patent application claims priority of the European patent application No. EP 3 165 782 A1, filed on Nov. 4, 2015.

FIELD OF THE INVENTION

The invention relates to a mechanical bearing containing a first component and a further component, wherein the mechanical bearing is designed such that the first component and the further component are able to execute a bearing movement relative to each other, wherein the first component or the further component contains a cermet or both contain a cermet. The invention further relates to an implantable medical device containing the mechanical bearing, in particular to a blood pump, and also to a use of a cermet for producing a mechanical bearing, and to a use of the mechanical bearing for supporting a component of an implantable medical device.

BACKGROUND OF THE INVENTION

The invention relates in particular to a heart assist system, also called a heart pump for short. In the prior art, a heart pump is used so that a heart that has become too weak is helped to pump blood. For this purpose, the heart pump is implanted in the body of the patient and is connected to the aorta and to the heart via blood-conveying tubes. The heart pump contains an impeller, which induces a strengthening of the blood flow. The impeller is driven by an electric motor. A control unit carried around outside the body, and batteries for supplying energy, are connected to the heart pump via a power cable that leads through the skin of the patient. The control unit and the batteries can be carried around by the patient on a belt or on shoulder straps. The impeller of the heart pump can be connected to the motor shaft. Various materials are used in the prior art to support the motor shaft and therefore the impeller, said materials each bringing with them specific disadvantages.

In the prior art, for example, ceramics are used as materials of a sliding bearing. Such ceramics have a low thermal conductivity. In the sliding bearing of the heart pump, this can lead to local heating and, consequently, to increased wear. Moreover, local heating of this kind can lead to clotting of the patient's blood. This can cause the death of the patient. Moreover, in the prior art, metals are used as materials for sliding bearings in heart pumps. However, metals have rather poor wear resistance. Moreover, in the prior art, coated sliding-bearing components are used in heart pumps. When using coated components, in particular in a mechanical bearing, there is always a residual risk of the coating peeling off. Coating parts which have peeled off, and which are released into the patient's body, may likewise lead to the death of the patient. Moreover, the prior art discloses the use of stones such as ruby as a bearing material. These have poor thermal conductivity, and therefore the comments made regarding the local heating of ceramics also apply here. Graphite, which is likewise known in the prior art as a bearing material, has low hardness and, consequently, is subject to considerable wear. The same applies to plastics as bearing materials. Sintered sliding bearings are also known in the prior art. During use, sintered and often porous sliding bearings in most cases result in mixed friction, since liquid can settle in the pores of the sintered material and thus serves as lubricant. If such a bearing is used in a heart pump, the liquid is blood. If blood settles in the pores, it can form clumps and cause growth of tissue around the bearing material, which can have a disadvantageous effect on the function of the heart pump and on the patient. Moreover, in the prior art, magnetic bearings with permanent magnets (DE 11 2006 002 413 T5) or combined magnetic/mechanical bearings (WO 98/00185A1, DE 196 25 300 A1) are also used in heart pumps. Such magnetic bearings have relatively low wear but are very elaborate to produce. Moreover, the magnetic field of the permanent magnets of the bearing can have a negative impact on other electromagnetic devices. Moreover, the precisely set magnetic field of the bearing can be disturbed by external electromagnetic fields, which can lead to misalignment of the magnetic bearing.

It is generally an object of the present invention to at least partially overcome a disadvantage arising from the prior art. It is an object of the invention to make available a heart pump which, when implanted in a patient, can lead to reduced clot formation during its operation. It is a further object of the invention to make available a mechanical bearing which is characterised by an as far as possible advantageous combination of low friction, high wear resistance and high thermal conductivity. It is a further object of the invention to make available a mechanical bearing which is as far as possible made only of biocompatible materials. It is a further object of the invention to make available a mechanical bearing which as far as possible contains no coating of the bearing components. It is a further object of the invention to make available a mechanical bearing which is characterised by a combination of the aforementioned features. It is a further object of the invention to make available an implantable medical appliance, for example a heart pump or a blood pump or both, with a mechanical bearing which achieves one of the aforementioned objects. Here, an actuator or an impeller is preferably supported in a movable manner by the mechanical bearing.

A contribution to the at least partial achievement of at least one of the above objects is made by the independent claims. The dependent claims set forth preferred embodiments that contribute to the at least partial achievement of at least one of the objects.

BRIEF SUMMARY OF THE INVENTION

A contribution to the achievement of at least one of the objects according to the invention is made by an embodiment 1 of a mechanical bearing 1 containing a first component and a further component, wherein the mechanical bearing is designed such that the first component and the further component are able to execute a bearing movement relative to each other, wherein the first component or the further component contains or is preferably composed of a cermet, or both components contain or are preferably composed of a cermet.

DETAILED DESCRIPTION OF THE INVENTION

Figure 1:
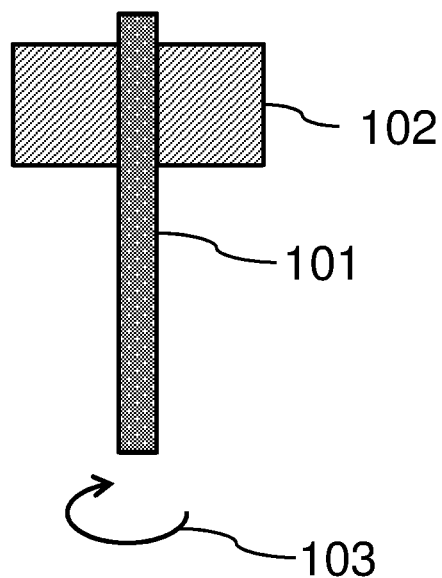
FIG. 1 shows a schematic cross-sectional view of a mechanical bearing according to the invention.

In an embodiment 2 according to the invention, the mechanical bearing 1 is designed according to the embodiment 1, wherein the cermet contains a metal in a proportion of at least 20% by weight, preferably at least 25% by weight, more preferably at least 30% by weight, in each case based on the total weight of the cermet. Some cermets have a maximum metal content of up to 90% by weight or up to 80% by weight or up to 70% by weight.

In an embodiment 3 according to the invention, the mechanical bearing 1 is designed according to the embodiment 1, wherein the cermet contains a metal in a metal fraction, wherein the metal fraction is a monotonically increasing function from a position on a straight line which runs through the cermet. Preferably, the first component contains a first bearing surface, and the further component contains a further bearing surface, wherein the first bearing surface rubs against the further bearing surface during execution of the bearing movement, wherein the further component contains the cermet, wherein the metal fraction of the cermet on the further bearing surface is minimal. Preferably, a ceramic fraction of the cermet is at a maximum on the further bearing surface.

In an embodiment 4 according to the invention, the mechanical bearing 1 is designed according to the embodiment 1, wherein the first component contains a first bearing surface, wherein the further component contains a further bearing surface, wherein the first bearing surface rubs against the further bearing surface during execution of the bearing movement, wherein the further component contains the cermet, wherein the cermet contains a metal in a metal fraction, wherein the metal fraction within the further component is a monotonically increasing function of a distance from the further bearing surface. A preferred cermet in this context is a gradient cermet, i.e. a cermet with a spatial gradient of the metal fraction. Here, the metal fraction is preferably at a minimum on the further bearing surface.

In an embodiment 5 according to the invention, the mechanical bearing 1 is designed according to the embodiment 3 or 4, wherein the metal fraction has a minimum in a range from 0 to 50% by weight, preferably 0 to 25% by weight, more preferably 0 to 10% by weight, still more preferably in a range from 0 to 4% by weight, in each case based on the weight of a spatial section of the cermet. Since the metal fraction increases monotonically with the distance from the further bearing surface, the cermet has the minimum of the metal fraction preferably on the further bearing surface. Accordingly, the spatial section of the cermet preferably contains the further bearing surface.

In an embodiment 6 according to the invention, the mechanical bearing 1 is designed according to one of the embodiments 3 to 5, wherein the metal fraction has a maximum in a range from 50 to 95% by weight, preferably 75 to 95% by weight, more preferably 90 to 95% by weight, in each case based on the weight of a spatial section of the cermet. Here, the spatial section preferably lies at a maximum distance from the further bearing surface.

In an embodiment 7 according to the invention, the mechanical bearing 1 is designed according to one of the embodiments 2 to 6, wherein the metal is biocompatible.

In an embodiment 8 according to the invention, the mechanical bearing 1 is designed according to one of the preceding embodiments, wherein the cermet contains, at maximum 80% by weight, preferably at maximum 75% by weight, more preferably at maximum 70% by weight, in each case based on the total weight of the cermet, of one chosen from the group consisting of ZrO, $Al_2O_3$, WC, SiN, carbon and AlN. A preferred carbon here is diamond. The above cermets are preferably doped, wherein the doping preferably lies in a range from 0.0001 to 5% by weight and particularly preferably in a range from 0.001 to 1% by weight, in each case based on the cermet. Preferred dopants are transition metals and rare earths, preferably chosen from the group consisting of Y, Ce, La, Nd, Sb, Ti or at least two thereof.

In an embodiment 9 according to the invention, the mechanical bearing 1 is designed according to one of the preceding embodiments, wherein the first component or the further component or both fulfil(s) one or more of the following criteria:
a) a hardness in a range from 400 to 3500 HV;
b) a specific thermal conductivity in a range from 30 to 800 W/(m·K);
c) contains no coating;
d) a porosity of less than 0.05, preferably less than 0.03, and particularly preferably less than 0.01.

It is particularly preferable here that the first component or the further component or both meet(s) one of the following feature combinations a)b)c)d), a), b), c), d), a)b), a),b),d). Under a), the hardness is preferably in a range from 400 to 600 HV, more preferably from 430 to 570 HV, more preferably from 470 to 530 HV. It is also particularly preferable that the hardness is in a range from 430 to 700 HV, more preferably from 430 to 670, more preferably from 470 to 630 HV, most preferably from 480 to 620 HV. Moreover, it is very particularly preferable that the hardness is in a range from 1000 to 3500 HV, more preferably from 1500 to 3300, more preferably from 1500 to 3300 HV, most preferably from 1800 to 3200 HV. Under b), the specific thermal conductivity is preferably in a range from 40 to 60 W/(m·K), more preferably from 43 to 57 W/(m·K), more preferably from 47 to 53 W/(m·K). Moreover, the specific thermal conductivity is particularly preferably in a range from 33 to 55 W/(m·K), more preferably from 37 to 50 W/(m·K), more preferably from 38 to 47 W/(m·K). Moreover, it is very particularly preferable that the specific thermal conductivity is in a range from 500 to 800 W/(m·K), more preferably from 550 to 780 W/(m·K), more preferably from 580 to 770 W/(m·K).

In an embodiment 10 according to the invention, the mechanical bearing 1 is designed according to one of the preceding embodiments, wherein the mechanical bearing has a coefficient of sliding friction in a range from 0.001 to 10, preferably from 0.01 to 5, more preferably from 0.05 to 0.25.

In an embodiment 11 according to the invention, the mechanical bearing 1 is designed according to one of the preceding embodiments, wherein the mechanical bearing is designed such that the bearing movement has one chosen from the group consisting of one degree of freedom, two degrees of freedom and three degrees of freedom or a combination of at least two thereof.

In an embodiment 12 according to the invention, the mechanical bearing 1 is designed according to one of the preceding embodiments, wherein the mechanical bearing is one chosen from the group consisting of a sliding bearing, a rolling bearing and a ball bearing, or a combination of at least two thereof. A sliding bearing is preferred.

In an embodiment 13 according to the invention, the mechanical bearing 1 is designed according to one of the preceding embodiments, wherein the mechanical bearing is a radial bearing or a linear bearing or both. A radial bearing is preferred.

In an embodiment 14 according to the invention, the mechanical bearing 1 is designed according to one of the preceding embodiments, wherein the first component is a shaft or an axle or both, preferably an axle. Here, a shaft is designed to transmit a torque. A shaft is preferably characterized in that it is a component with a drive function. Moreover, an axle is characterized in that it is a component for carrying or supporting rotatable components or for doing both. A preferred axle has no drive function.

In an embodiment 15 according to the invention, the mechanical bearing 1 is designed according to one of the embodiments 1 to 13, wherein the first component is a shaft, wherein the shaft is driven by a magnetic field. The shaft is preferably driven without contact by a drive unit, preferably an electric motor.

A contribution to the achievement of at least one of the objects according to the invention is made by an embodiment 1 of an implantable medical device 1 containing the mechanical bearing 1 according to one of the embodiments 1 to 15.

In an embodiment 2 according to the invention, the implantable medical device 1 is designed according to the embodiment 1, wherein the implantable medical device contains a motor. Preferably, the motor is at least partially housed in a hermetically tight manner.

In an embodiment 3 according to the invention, the implantable medical device 1 is designed according to the embodiment 1 or 2, wherein the mechanical bearing supports an impeller.

In an embodiment 4 according to the invention, the implantable medical device 1 is designed according to one of the embodiments 1 to 3, wherein the implantable medical device is a pump or an actuator or both. A preferred pump is a blood pump or a heart pump or both.

A contribution to the achievement of at least one of the objects according to the invention is made by an embodiment 1 of a method 1 containing as method steps:
a) providing a housing; and
b) introducing a movable component into the housing;

wherein the housing is made of a biocompatible material, wherein the movable component is mounted movably in the housing by means of the mechanical bearing 1 according to one of its embodiments 1 to 15. A preferred movable component is an impeller.

A contribution to the achievement of at least one of the objects according to the invention is made by an embodiment 1 of an apparatus 1 obtainable by the method 1 according to its embodiment 1. A preferred apparatus is an implantable medical device.

A contribution to the achievement of at least one of the objects according to the invention is made by an embodiment 1 of a method 2 containing as method steps:
a) providing the implantable medical device 1 according to one of its embodiments 1 to 4 or the apparatus 1 according to its embodiment 1; and
b) introducing the implantable medical device 1 or the apparatus 1 into a eukaryotic organism.

A contribution to the achievement of at least one of the objects according to the invention is made by an embodiment 1 of a use 1 of a cermet for producing a mechanical bearing.

A contribution to the achievement of at least one of the objects according to the invention is made by an embodiment 1 of a use 2 of the mechanical bearing according to one of its embodiments 1 to 15 for supporting a component of an implantable medical device.

A contribution to the achievement of at least one of the objects according to the invention is made by an embodiment 1 of a use 3 of the implantable medical device 1 according to one of its embodiments 1 to 4 or of the apparatus 1 according to its embodiment 1 for treatment or therapy of a eukaryotic organism. A preferred treatment or therapy is that of a cardiac insufficiency. A cardiac insufficiency with pump failure is preferred in this case. Particularly preferred are cardiac insufficiencies of classes III and IV, very particularly preferably of class IV, according to the classification of the New York Heart Association (NY HA).

Preferred configurations of constituents of a category according to the invention, in particular of the mechanical bearing according to the invention, of the implantable medical device according to the invention, and of the method according to the invention, are likewise preferred for corresponding constituents, or constituents of the same name, of the respectively other categories according to the invention.

Mechanical Bearing

In a mechanical bearing, the bearing movement causes a mechanical friction, preferably a sliding friction or a rolling friction or both. In addition, the mechanical bearing according to the invention does not have to be purely mechanical; in particular, the mechanical bearing according to the invention can be a combined mechanical/magnetic bearing. For this purpose, the bearing can contain one or more permanent magnets, preferably at least two permanent magnetics oriented with opposite polarity to each other.

Metal

All metals familiar to a person skilled in the art may be considered here if they have good compatibility with eukaryotic tissue. A preferred metal according to the invention is preferably chosen from the group consisting of platinum, iridium, niobium, palladium, iron, stainless steel, cobalt-chromium alloy, molybdenum, tantalum, tungsten, titanium, cobalt and zirconium, or a combination of at least two thereof. A preferred combination here is an alloy. A preferred stainless steel is a stainless steel 316L. A preferred metal is biocompatible. A preferred alloy is biocompatible. A preferred biocompatible metal is one chosen from the group consisting of palladium, rhodium, ruthenium, molybdenum, platinum, iridium, tungsten, gold, titanium, niobium and tantalum, or a combination of at least two thereof.

Cermet

According to the invention, "cermet" designates a composite consisting of one or more ceramics in at least one metal matrix or a composite consisting of one or more metals in at least one ceramic matrix, or both. To produce a cermet, for example, a mixture of at least one ceramic powder and of at least one metallic powder can be used to which, for example, it is possible to add at least one binder and, if appropriate, at least one solvent. The one or more ceramic powders of the cermet preferably have a mean grain size of less than 10 μm, preferably less than 5 μm, particularly preferably less than 3 μm. The one or more metallic powders of the cermet preferably have a mean grain size of less than 15 µm, preferably less than 10 µm, particularly preferably less than 5 µm. The mean grain size here is regarded in particular as the median value or $D_{50}$ value of the grain size distribution. The $D_{50}$ value describes the value at which 50% of the grains of the ceramic powder and/or of the metallic powder are finer than the $D_{50}$ value. A preferred cermet has a high specific conductivity, which preferably measures at least 1 S/m, more preferably at least 100 S/m, more preferably at least $10^3$ S/m, more preferably at least $10^4$ S/m, still more preferably at least $10^5$ S/m, and most preferably at least $10^6$ S/m.

The at least one ceramic component of a cermet according to the invention preferably contains a ceramic according to the invention. The at least one metallic component of a cermet according to the invention preferably contains one chosen from the group consisting of platinum, iridium, niobium, palladium, iron, stainless steel, cobalt-chromium alloy, molybdenum, tantalum, tungsten, titanium, cobalt and zirconium, or a combination of at least two thereof. A preferred combination of these is an alloy. A preferred stainless steel is a stainless steel 316L. An electrically conductive connection is generally established in the cermet when the metal content lies above the so-called percolation threshold, at which the metal particles in the sintered cermet are connected to one another at least at points, such that electrical conduction is permitted. Experience shows that, for this purpose, depending on the material chosen, the metal content has to be at least 25% by volume, preferably at least 32% by volume, most preferably at least 38% by volume, in each case based on the total volume of the cermet. In a particularly preferred cermet, the ceramic component is diamond or $Al_2O_3$, and the metallic component is platinum.

Ceramic

A ceramic according to the invention can be any ceramic that a person skilled in the art would choose for the use according to the invention. The ceramic is preferably chosen from the group consisting of an oxide ceramic, a silicate ceramic, a non-oxide ceramic and an elemental ceramic, or a mixture of at least two thereof.

The oxide ceramic is preferably chosen from the group consisting of a metal oxide, a semimetal oxide, or a mixture thereof. The metal of the metal oxide can be chosen from the group consisting of aluminium, beryllium, barium, calcium, magnesium, sodium, potassium, iron, zirconium, titanium, or a mixture of at least two thereof. The metal oxide is preferably chosen from the group consisting of aluminium oxide ($Al_2O_3$), magnesium oxide (MgO), zirconium oxide ($ZrO_2$), yttrium oxide ($Y_2O_3$), aluminium titanate ($Al_2TiO_5$), a piezoceramic such as lead zirconate ($PbZrO_3$), lead titanate ($PbTiO_3$) and lead zirconate titanate (PZT), or a mixture of at least two thereof. The semimetal of the semimetal oxide is preferably chosen from the group consisting of boron, silicone, arsenic, tellurium, or a mixture of at least two thereof. A further preferred oxide ceramic includes one chosen from the group consisting of zirconia-toughened aluminium oxide (ZTA; $Al_2O_3/ZrO_2$), yttria-toughened zirconia (Y-TZP), barium(Zr,Ti)oxide, barium(Ce,Ti)oxide or a combination of at least two thereof.

The silicate ceramic is preferably chosen from the group consisting of a steatite ($Mg_3[Si_4O_{10}(OH)_2]$), cordierite ($Mg,Fe^{2+})_2(Al_2Si)[Al_2Si_4O_{18}]$), mullite ($Al_2Al_{2+2x}Si_{2-2x}O_{10-x}$ where x=oxygen vacancies per unit cell), feldspar ($Ba,Ca,Na,K,NH_4)(Al,B,Si)_4O_8$), or a mixture of at least two thereof.

The nonoxide ceramic can be chosen from the group consisting of a carbide, a nitride or a mixture thereof. The carbide can be chosen from the group consisting of silicon carbide (SiC), boron carbide ($B_4C$), titanium carbide (TiC), tungsten carbide, cementite ($Fe_3C$). The nitride can be chosen from the group consisting of silicon nitride ($Si_3N_4$), aluminium nitride (AlN), titanium nitride (TiN), silicon aluminium oxynitride (SIALON), or a mixture of at least two thereof. A further preferred nonoxide ceramic is sodium potassium niobate.

The elemental ceramic is preferably carbon, particularly preferably diamond. To produce a cermet which contains an elemental ceramic as the ceramic component, a diamond powder is preferably mixed with a metal powder. Such a cermet with an elemental ceramic as the ceramic component is characterised by a particularly preferred combination of a high degree of hardness and a high specific thermal conductivity.

Biocompatible Material

A preferred biocompatible material is one chosen from the group consisting of biotolerant, bioinert and bioactive, or a combination of at least two thereof.

Hermetically Tight

In the context of the invention, the term "hermetically tight" can signify that, with correct use over customary periods of time (for example 5 to 10 years), moisture or gases or both cannot be exchanged, or can be only minimally exchanged, through the hermetically tight barrier, for example the housing, between interior and exterior. A physical variable that can describe for example a permeation of gases or moisture or both through the barrier is the so-called leak rate, which can be determined by leak tests, for example. Corresponding leak tests can be carried out, for example, with helium leak testers and/or mass spectrometers and are specified in the standard Mil-STD-883G Method 1014. The maximum permissible helium leak rate is in this case fixed according to the internal volume of the device to be tested, here for example the internal volume of the housing. On the basis of the methods specified in MIL-STD-883G Method 1014, in paragraph 3.1, and taking into consideration the volumes and cavities of the devices to be tested that are encountered in the use of the present invention, these maximum permissible helium leak rates can be, for example, from $1\times10^{-8}$ atm×cm$^3$/sec to $1\times10^{-7}$ atm×cm$^3$/sec. Within the context of the invention, the term "hermetically sealed" may in particular mean that the barrier has a helium leak rate of less than $1\times10^{-7}$ atm×cm$^3$/sec. In an advantageous embodiment, the helium leak rate can be less than $1\times10^{-8}$ atm×cm$^3$/sec, in particular less than $1\times10^{-9}$ atm×cm$^3$/sec.

For the purpose of standardization, the stated helium leak rates can also be converted into the equivalent standard air leak rate. The definition of the equivalent standard air leak rate and the conversion are specified in the standard ISO 3530.

On account of the type of use of implantable medical devices, the hermetic sealing and biocompatibility of the electrical components, for example of the motor, is generally one of the primary requirements. The implantable medical device proposed here can in particular be fitted into a body of a human or animal user, in particular of a patient. As a result, the device is generally exposed to a bodily fluid such as blood. It is therefore generally important that bodily fluid does not get into electrical components and that liquid does not escape from the electrical components. In order to ensure this, the housing of the electrical components should have an impermeability that is as complete as possible, in particular with respect to bodily fluids.

Eukaryotic Organism

A preferred eukaryotic organism is an animal organism or a human organism or both.

Measuring Methods

The following measuring methods were used in the context of the invention. Unless otherwise stated, the measurements were carried out at an ambient temperature of 25° C., an ambient air pressure of 100 kPa (0.986 atm) and a relative air humidity of 50%.

Biocompatibility

The biocompatibility is determined in accordance with ISO 10993-4:2002.

Hardness

The hardness was measured in accordance with DIN EN ISO 6507-1 to -4. For this purpose, a ZHVµ Mikro Vickers hardness tester from Zwick Roell AG, Ulm, Germany was used, along with the associated software. The Vickers pyramid 136° was used as the indenter. The chosen load was 2000 g and the retention time 15 seconds.

Specific Thermal Conductivity

The specific thermal conductivity was measured using an LFA 467 HyperFlash Light Flash apparatus from NETZSCH-Gerätebau GmbH, Selb/Bayern, Germany. A cylindrical test body with a diameter of 10 mm and a thickness of 5 mm was used for the measurement. The measurement was carried out under vacuum and in a temperature range of 10 to 50° C.

Coefficient of Sliding Friction

The coefficient of sliding friction is defined as $\mu = F_R/F_N$, where $F_R$ is the frictional force and $F_N$ is the normal force. The definition of $\mu$ is accordingly obtained by a measurement of a force-travel profile of a friction process. Firstly, 2 specimens, each of them with plane parallel surfaces, are produced from the material to be tested. The friction is measured under dry friction. The measurement is also carried out with a Zwick Z0.5 test machine from Zwick GmbH & Co. KG, Ulm, and with the associated software. The measurement set-up consists of a single-axle motor stage and a carriage. The sliding partners are secured on the motor stage and on the carriage and moved against each other. The carriage is initially moved until the force sensor responds, and it is then released again. It is only after a rest period that the actual recording of the frictional force $F_R$ takes place. In order to eliminate acceleration forces, $F_R$ is not measured on the motor stage but instead on the immovable carriage. For evaluation, the normal force $F_N$ also needs to be known. Here, $F_N$ is fixed, by the pressure of the two specimens against each other, at a value of 10 to 50 N/mm². For the sliding friction force $F_R$, the mean value during a fixed length of travel is used.

Porosity

To measure the porosity, metallographic ground specimens were firstly produced by embedding in epoxy resin, grinding with SiC paper of successively smaller grain size, and polishing with a diamond paste. The outermost layer of each specimen was removed by etching of the specimen. Thereafter, images of the specimen surface thus treated were taken using a light microscope and an electron microscope. The highest possible contrast between the pores of the specimen and the material (metal and ceramic) was to be obtained here. To evaluate the images, these grayscale images were converted into binary images by Otsu's method. That is to say, the image pixels were each assigned to a pore or to the specimen material by means of a threshold value. The porosity was then determined using the binary images, as a quotient from the number of pixels that represent pores and the total number of the pixels per image. The porosity was determined here as an arithmetic mean from 5 images, each recorded on 5 ground specimens.

Clot Formation

To determine the clot formation in a heart pump, a sufficient quantity of blood (up to 2 liters) was firstly taken from a pig (1 animal per test). This blood was used to carry out the in vitro test as per "In-vitro-Teststand für die Untersuchung der Thrombenbildung in Blutpumpen und anderen blutkontaktierten Systemen" [In vitro testing for the investigation of clot formation in blood pumps and other systems in contact with blood] (Biomedizinische Technik/Biomedical Engineering, volume 37, no. s1, pages 266-268, 1992, ISSN (online) 1862-278X, ISSN (print) 0013-5585, DOI: 10.1515/bmte.1992.37.s1.266, July 2009 online) by H. Schima et al. Here, the heart pump to be tested was in each case used in the described test set-up. The test duration selected was 3 hours. If it was found that the blood sampling was incorrect during the conduct of the test, this test was rejected. After the test had been carried out according to the cited source, the tested heart pump was dismantled and the individual parts were examined for clots. Identified clots were measured in respect of their size.

EXAMPLES

The invention is set out in more detail below through examples and drawings; the examples and drawings do not limit the invention. Unless otherwise stated, the drawings are not to scale.

Example According to the Invention

Firstly, a bearing socket of a mechanical bearing for the impeller of a commercially available heart pump was produced from materials according to the invention. For this purpose, consideration is given to heart pumps such as HeartMate II from Thoratec Europe Limited, Cambridgeshire, United Kingdom; HVAD (VAD—Ventricular Assist System) from HeartWare GmbH, Hannover, Germany; or INCOR from Berlin Heart GmbH, Berlin, Germany. In this connection, the HeartMate II is a very widely used product.

To produce the bearing socket according to the invention, cermet pastes were initially produced from $Al_2O_3$, platinum and organic vehicle. Different amounts of platinum powder were used for the different cermet pastes. For the various cermet pastes, 3 to 60 g of platinum powder were in each case mixed with 24 g of $Al_2O_3$ powder and an organic vehicle based on ethyl cellulose, and this mixture was homogenized in a three-roll mill. The pastes thus obtained had a viscosity in the range from 250 to 500 Pa*s and a fineness of grind (FoG) of less than 10 µm. It was to be ensured here that the pastes were suitable for printing on account of their rheological properties (in particular viscosity).

The detailed paste production process is explained below. The components were mixed manually in a beaker glass. This pre-mixed paste was homogenized in an Exakt E80 (from EXAKT Advanced Technologies GmbH) three-roll mill with stainless steel rollers. The paste was fed to the mill repeatedly, wherein the gaps (gap 1 between the first and second roller, gap 2 between the second and third roller) between the rollers were reduced. The gaps were able to be regulated here either via the gap width (distance control) or via the pressure between the rollers (pressure control). The first milling steps were carried out with distance control, the final milling steps with pressure control. The values that were used in the individual milling steps are listed below. Here, distance and pressure were each identical for gap 1 and gap 2.

Milling steps 1 and 2: distance control 20 μm
Milling steps 3 and 4: distance control 15 μm
Milling steps 5 and 6: distance control 10 μm
Milling steps 7 and 8: distance control 5 μm
Milling steps 9, 10 and 11: pressure control 10 N/mm
Milling steps 12, 13 and 14: pressure control 12.5 N/mm
Milling steps 15, 16 and 17: pressure control 15 N/mm In further examples according to the invention, commercially available cermet pastes such as CL11-8822 (from Heraeus Precious Metals North America, Conshohocken LLC) were used.

By means of 3D screen printing, a green body was produced from the cermet pastes with different platinum fractions. The procedure here was such that the different pastes with correspondingly different platinum and $Al_2O_3$ fractions were built up in several layers by screen printing, to form the green body. Here, a gradient of the metal fraction was realized in a direction perpendicular to the layers. The direction of the gradient was chosen such that a high ceramic fraction of 85 to 95% by weight was obtained near the bearing surface of the bearing socket and such that a sufficiently high metal fraction was obtained ca. 50 μm farther into the green body. The transition between the different areas had to be smooth here, so that no delamination takes place on account of the different material properties (e.g. thermal expansion).

The green body thus obtained was sintered at ca. 1500° C. To further reduce the porosity to below 0.01, the component obtained was subjected to hot isostatic pressing. By subsequent grinding and polishing, the obtained bearing part was machined to fit the above heart pump. The bearing socket is 70% by weight platinum and 30% by weight $Al_2O_3$, in each case based on the total weight of the bearing socket. Here, the metal fraction has its minimum of 5% by weight on the surface of the bearing socket, which supports the shaft with sliding friction, and has its maximum of 90% by weight at a maximum distance from this surface.

Moreover, a commercially available heart pump was provided. It was opened and the customary bearing was removed. The bearing socket in the bearing was replaced by the bearing socket according to the invention, produced in accordance SU with the above details, and the bearing was then reinstalled in the heart pump. The heart pump thus obtained was then subjected to tests.

Comparison Examples not According to the Invention

For this purpose, a commercially available heart pump was tested with the customary bearing. Moreover, bearings made of ceramic, metal, plastic and stone were tested in this heart pump.

Assessment

By comparing the example according to the invention against the comparison examples, it was found that the bearing according to the invention in the heart pump, when compared to the bearings not according to the invention, has an advantageous combination of low friction, high wear resistance and high thermal conductivity. In addition, the bearing according to the invention is made of biocompatible materials. Moreover, the test described above for clot formation was carried out. This showed that heart pumps with the bearing according to the invention form fewer and smaller clots.

FIG. 1 shows a schematic cross-sectional view of a mechanical bearing 100 according to the invention. The mechanical bearing 100 is a sliding bearing, more precisely a radial bearing. The mechanical bearing 100 contains a first component 101, which is a shaft of an electric motor or an axle, and a further component 102, which is a bearing shell. The mechanical bearing 100 is designed such that the shaft/axle 101 and the bearing shell 102 are able to execute a bearing movement 103 relative to each other, a rotation of the shaft/axle 101. The bearing shell 102 is made of a cermet. The cermet is 30% by weight titanium and 70% by weight $Al_2O_3$, in each case based on the total weight of the cermet. The cermet is biocompatible.

Figure 2A:
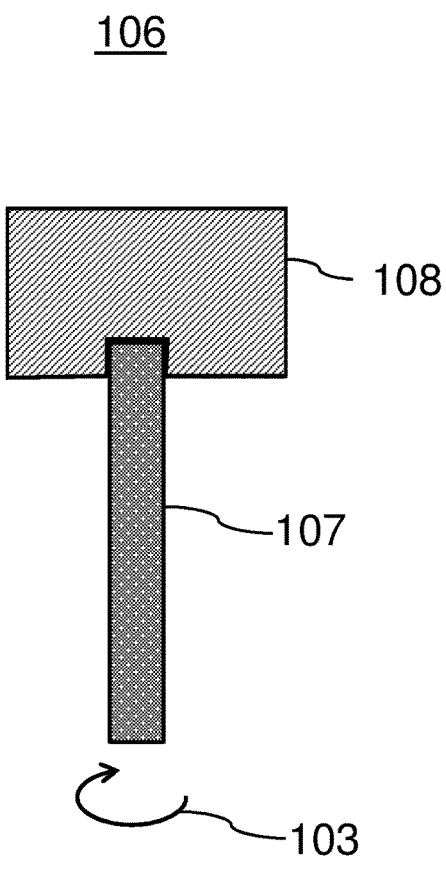
FIG. 2a) shows a schematic cross-sectional view of a further mechanical bearing according to the invention.

FIG. 2a) shows a schematic cross-sectional view of a further mechanical bearing 106 according to the invention. The mechanical bearing 106 is a sliding bearing, more precisely an axial bearing. The mechanical bearing 106 contains a first component 107, which is a shaft of an electric motor or an axle, and a further component 108, which is a bearing shell. The mechanical bearing 106 is designed such that the shaft/axle 107 and the bearing shell 108 are able to execute a bearing movement 103 relative to each other, a rotation of the shaft/axle 107. The bearing shell 108 is made of a cermet. The cermet is 25% by weight palladium and 75% by weight ZrO, in each case based on the total weight of the cermet. The cermet is biocompatible.

Figure 2B:
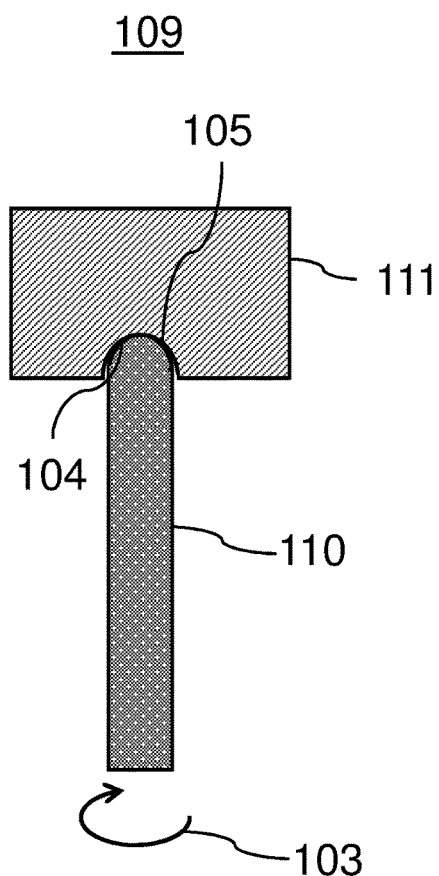
FIG. 2b) shows a schematic cross-sectional view of a further mechanical bearing according to the invention.

FIG. 2b) shows a schematic cross-sectional view of a further mechanical bearing 109 according to the invention. The mechanical bearing 109 is a sliding bearing, more precisely an axial bearing. The mechanical bearing 109 contains a first component 110, which is a shaft of an electric motor or an axle, and a further component 111, which is a bearing shell. The mechanical bearing 109 is designed such that the shaft/axle 110 and the bearing shell 111 are able to execute a bearing movement 103 relative to each other, a rotation of the shaft/axle 110. During the execution of the bearing movement, a first bearing surface 104 of the shaft 110 rubs against a further bearing surface 105 of the bearing shell 111. The bearing shell 111 is made of a cermet with a spatial gradient of a metal fraction. The metal here is platinum. A ceramic component of the cermet is $Al_2O_3$. The metal fraction at the further bearing surface is 0% by weight based on the weight of a spatial section of the cermet which contains the further bearing surface 105 and contains no point within the cermet farther than 1 mm from the further bearing surface 105. The metal fraction of the cermet becomes greater with a distance from the further bearing surface 105. A maximum of the metal fraction in the cermet is 90% by weight relative to the weight of a spatial section of the cermet.

Figure 3:
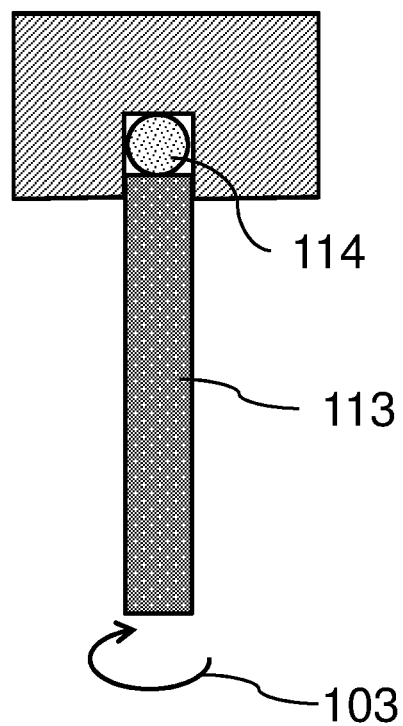
FIG. 3 shows a schematic cross-sectional view of a further mechanical bearing according to the invention.

FIG. 3 shows a schematic cross-sectional view of a further mechanical bearing 112 according to the invention. The mechanical bearing 112 is an axial ball bearing. The mechanical bearing 112 contains a first component 113, which is a shaft of an electric motor or an axle, and a further component 114, which is a ball in a bearing shell. The mechanical bearing 112 is designed such that the shaft/axle 113 is able to execute a bearing movement 103 relative to the ball 114 and the bearing shell, a rotation of the shaft 113. The ball 114 and the bearing shell are each made of a cermet. The cermet is 28% by weight titanium and 72% by weight AlN, in each case based on the total weight of the cermet. The cermet is biocompatible.

Figure 4:
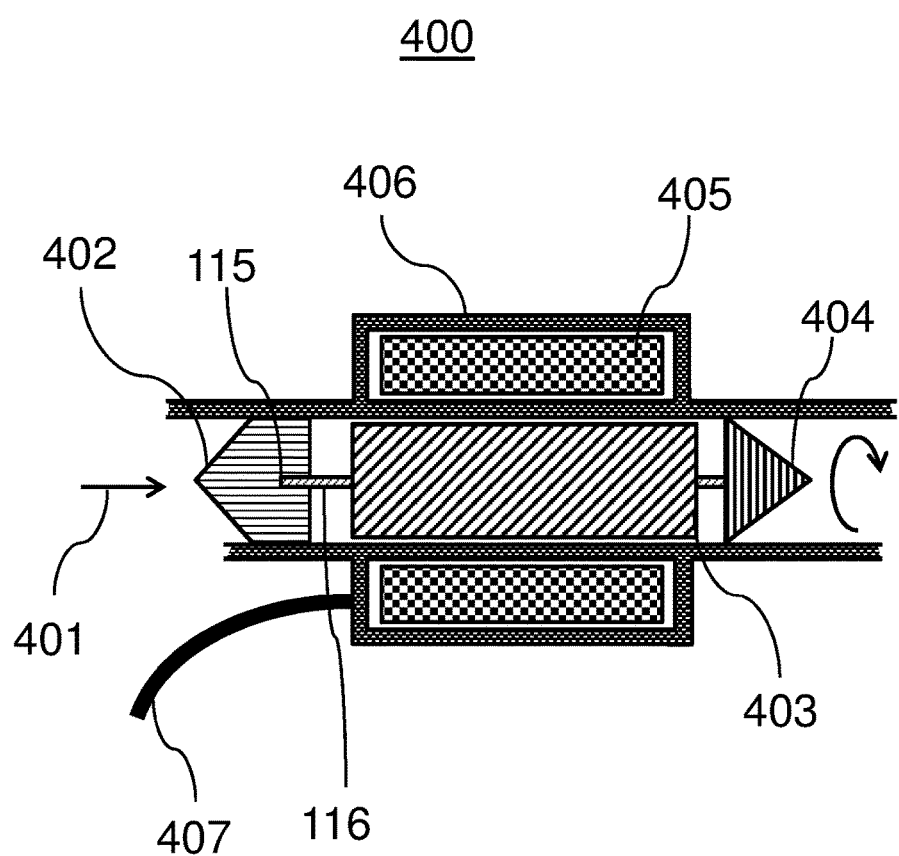
FIG. 4 shows a schematic cross-sectional view of an implantable medical device according to the invention.

FIG. 4 shows a schematic cross-sectional view of an implantable medical device 400 according to the invention, which is a heart pump. Blood, which flows in the direction of blood flow 401 into the heart pump 400, initially passes through a flow straightener 402, which reduces turbulence of the blood flow. A shaft 116 carries an impeller 403. The shaft 116 and thus the impeller 403 are mounted in a sliding bearing 115 according to the invention. The impeller strengthens the flow of the blood and thus assists the pumping function of the heart. The heart pump 400 moreover contains a diffusor 404. The shaft 116 is driven by an electric motor, of which the stator 405 is accommodated in a hermetically sealed manner in a housing 406. The electric motor here drives the shaft 101 without contact, by means of an electromagnetic field. The electric motor is operated with current via a power cable 407.

Figure 5:
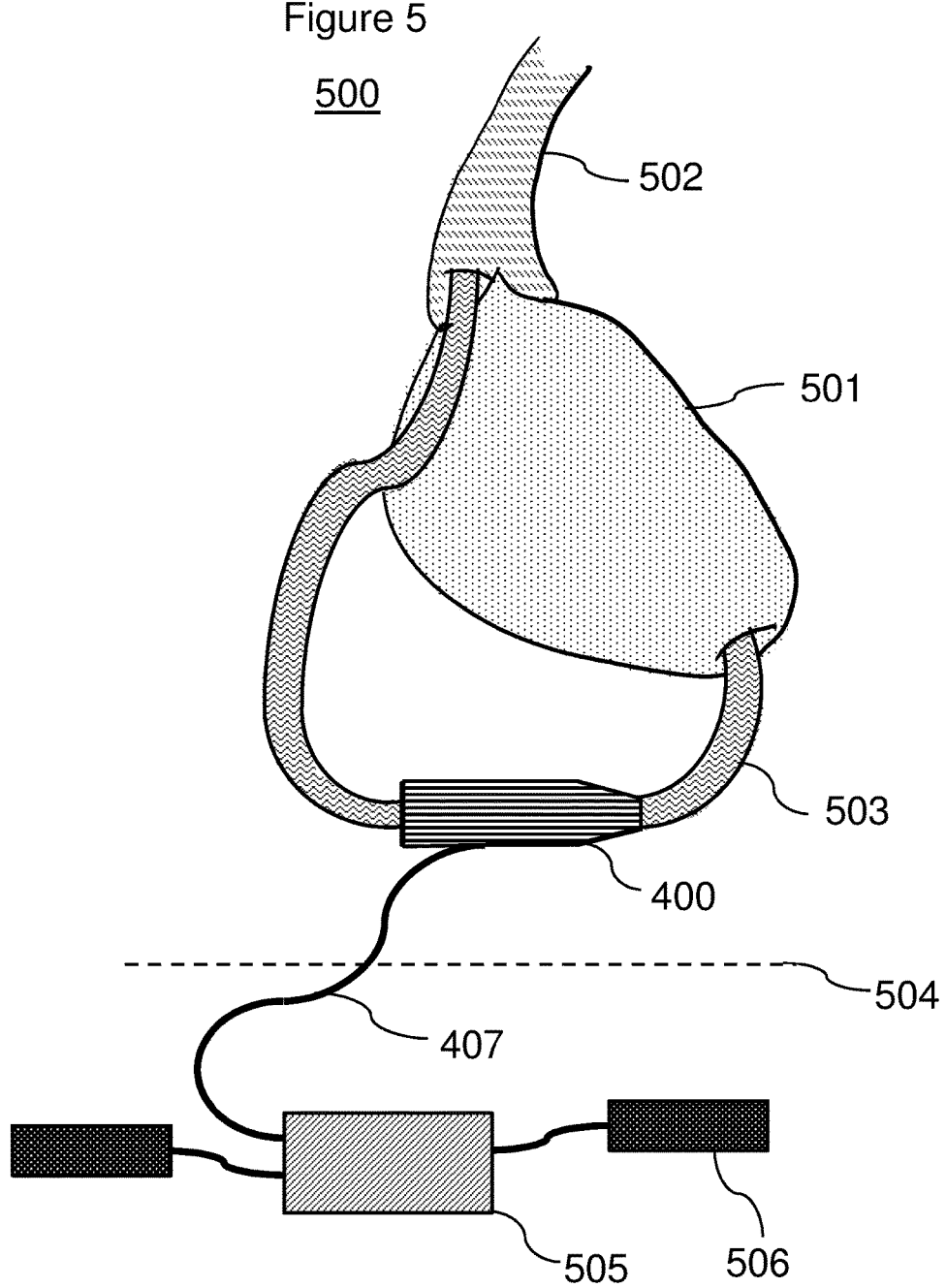
FIG. 5 shows a schematic view of a left-ventricular heart assist system with a heart pump according to the invention.

FIG. 5 shows a schematic view of a left-ventricular heart assist system 500 with an implanted heart pump 400 according to the invention as per FIG. 4. The heart pump 400 is attached by a blood-conveying tube 503 to the apex of the heart 501 and via a further blood-conveying tube 503 to the aorta 502. A power cable 407, which supplies current to the heart pump 400, runs from inside the body of the patient out through a skin boundary 504 to a control unit 505, which controls the heart pump 400. The control unit 505 can be worn on a belt by the patient. The control unit 505 is connected by further power cables 407 to two batteries 506. The patient can carry each of the batteries 506 in a respective shoulder strap.

Figure 6:
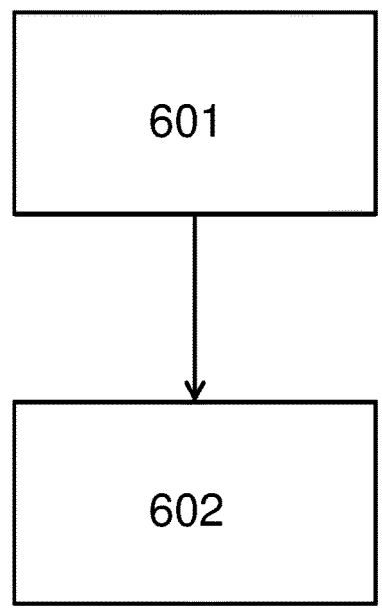
FIG. 6 shows a flow chart of a method according to the invention.

FIG. 6 shows a flow chart of a method 600 according to the invention for producing a heart pump 400. In a method step a) 601, a housing made of titanium and with a flow channel is made available. In a method step b) 602, a shaft/axle 101 with an impeller 402 is introduced into the flow channel. The shaft/axle 101 is mounted in the flow channel with the radial bearing as per FIG. 1.

LIST OF REFERENCE SIGNS 100 mechanical bearing according to the invention
101 first component/shaft/axle
102 further component
103 bearing movement
104 first bearing surface
105 further bearing surface
106 mechanical bearing according to the invention
107 first component/shaft/axle
108 further component
109 mechanical bearing according to the invention
110 first component/shaft/axle
111 further component
112 mechanical bearing according to the invention
113 first component/shaft/axle
114 further component
115 mechanical bearing according to the invention
116 first component/shaft/axle
400 implantable medical device according to the invention/heart pump
401 direction of blood flow
402 flow straightener
403 impeller
404 diffusor
405 motor stator
406 housing
407 power cable
500 left-ventricular heart assist system
501 heart
502 aorta
503 tube
504 skin boundary
505 control unit
506 battery
600 method according to the invention
601 method step a)
602 method step b)

The invention claimed is:

1. A mechanical bearing containing a first component and a further component, wherein the mechanical bearing is designed such that the first component and the further component are able to execute a bearing movement relative to each other, wherein the first component or the further component contains a cermet or both contain a cermet, wherein the cermet contains a metal in a proportion of at least 20% by weight relative to the total weight of the cermet, wherein the metal is biocompatible.

2. The mechanical bearing according to claim 1, wherein the cermet contains a metal in a metal fraction, wherein the metal fraction is a monotonically increasing function from a position on a straight line which runs through the cermet.

3. The mechanical bearing according to claim 2, wherein the metal fraction has a minimum in a range from 0 to 50% by weight based on the weight of a spatial section of the cermet.

4. The mechanical bearing according to claim 2, wherein the metal fraction has a maximum in a range from 50 to 95% by weight based on the weight of a spatial section of the cermet.

5. An implantable medical device containing the mechanical bearing according to claim 1.

6. A method containing as method steps:
 a) providing the implantable medical device according to claim 5, and
 b) introducing the implantable medical device or the apparatus into an eukaryotic organism.

7. A method containing as method steps:
 a) providing a housing; and
 b) introducing a movable component into the housing;
 wherein the housing is made of a biocompatible material, wherein the movable component is mounted movably in the housing by means of the mechanical bearing according to claim 1.

* * * * *